(12) United States Patent
Minarini (10) Patent No.: US 10,499,906 B2
(45) Date of Patent: Dec. 10, 2019

(54) AIDING AND GUIDING INSTRUMENT FOR SURGICAL SUTURES (71) Applicant: MED-EUROPE EUROPEAN MEDICAL SUPPLIES S.R.L., Bologna (IT)

(72) Inventor: Marco Minarini, San Lazzaro di Savena (IT)

(73) Assignee: MED-EUROPE EUROPEAN MEDICAL SUPPLIES S.R.L., Bologna (IT)

( * ) Notice: Subject to any disclaimer, the term of this patent is extended or adjusted under 35 U.S.C. 154(b) by 366 days.

(21) Appl. No.: 15/317,800

(22) PCT Filed: Jun. 5, 2015

(86) PCT No.: PCT/EP2015/062559
§ 371 (c)(1),
(2) Date: Dec. 9, 2016

(87) PCT Pub. No.: WO2015/189100
PCT Pub. Date: Dec. 17, 2015

(65) Prior Publication Data
US 2017/0112490 A1 Apr. 27, 2017

(30) Foreign Application Priority Data

Jun. 12, 2014 (IT) ................. BO140056 U (51) Int. Cl.
*A61B 17/04* (2006.01)
*A61B 17/06* (2006.01)
*A61B 17/00* (2006.01)

(52) U.S. Cl.
CPC .... *A61B 17/0482* (2013.01); *A61B 17/06061* (2013.01); *A61B 2017/00946* (2013.01)

(58) Field of Classification Search
CPC .................. A61B 17/0482; A61B 17/06061
See application file for complete search history.

(56) References Cited

U.S. PATENT DOCUMENTS

2003/0055439 A1* 3/2003 Koseki ............ A61B 17/06061
606/148
2010/0010475 A1* 1/2010 Teirstein ............... A61M 25/02
604/528

FOREIGN PATENT DOCUMENTS

CN 102614001 B 1/2014

OTHER PUBLICATIONS

International Search Report dated Sep. 3, 2015 re: Application No. PCT/EP2015/062559; pp. 1-3; citing: US 2003/055439 A1, CN 102 614 001 B and US 2010/010475 A1.

(Continued)

*Primary Examiner* — Richard G Louis
(74) *Attorney, Agent, or Firm* — Cantor Colburn LLP (57) ABSTRACT

An aiding and guiding instrument for surgical sutures includes a frame that can be rested on a patient proximate to a wound to be sutured and/or to flaps of body tissue and/or prosthetic tissue to be mutually fixed. The frame defines, on the other side from the area configured to be placed on the patient, a plurality of raised portions arranged in series. At least some of the raised portions are mutually spaced to define respective seats for accommodating blocks. In the gap between each block and each contiguous raised portion, it is possible to temporarily stably accommodate a portion of a suture thread. At least one portion of the frame, associated with the raised portions and seats, can be plastically deformed to maintain the shape obtained following a deformation imparted by a user, and freely select the frame shape, and of the mutual arrangement of the raised portions and blocks.

9 Claims, 5 Drawing Sheets (56) References Cited

OTHER PUBLICATIONS

Written Opinion dated Sep. 3, 2015 re: Application No. PCT/EP2015/062559; pp. 1-6; citing: US 2003/055439 A1, CN 102 614 001 B and US 2010/010475 A1.

* cited by examiner

AIDING AND GUIDING INSTRUMENT FOR SURGICAL SUTURES

CROSS-REFERENCE TO RELATED APPLICATIONS

This application is related to and claims the benefit of Italian Patent Application No. BO2014U000056, filed on Jun. 12, 2014, the contents of which are herein incorporated by reference in their entirety.

TECHNICAL FIELD

The present disclosure relates to an aiding and guiding instrument for surgical sutures.

BACKGROUND

As is known, the term "surgical suture" identifies a set of surgical procedures of various types, all of which are aimed at the stable bringing together of the two flaps of a wound, or in any case of two previously-cut flaps of body tissue, in order to favor their healing Such sets of procedures likewise includes those whose purpose is to fix prosthetic material of various types (e.g., vascular or valvular) to body tissues, for the substitution or reinforcement of natural structures with prosthetic material.

Although recently various alternative methods have been developed of carrying out such sutures (such as, for example, those involving the use of adhesives or plasters) in one of the most widespread techniques, the medical personnel passes one or more threads (usually made of polymeric material) through the flaps of tissue (body or prosthetic) to be brought together, in order to then form surgical knots and stitches, which keep the flaps in the desired position (brought together) during the healing process.

Moreover, for fixing suturable prosthetic materials to the natural tissues of the patient, the use of sutures of the type described above is made mandatory by the reference standards, and thus it cannot be substituted with one of the other methods cited.

In this regard, it should be noted that a first macro categorization of sutures makes a distinction between "continuous" sutures, in which the same thread is used in all the stitches without interruption, and "interrupted" sutures, in which the thread is cut after each stitch, or different threads are used, each of which goes to form a respective stitch.

It is the "interrupted" sutures which are used most frequently in cardiac surgery and thoracotomy operations, when what is necessary is reconstruction, anastomosis, or the fixing of prosthetic material to blood vessels or to intracardiac structures such as, for example, natural valve rings.

In such circumstances therefore, the surgeon first of all inserts, in sequence, a series of threads along the tissues (natural or prosthetic) to be joined, passing through the flaps at stitches which are conveniently spaced apart, so as to ensure an optimal join and without causing excessive trauma to the tissues.

In a second step, the surgeon (or other technician) grasps the mutually opposite ends of each thread, linking them and tying one or more respective knots (generally five or six): the repetition of such operation, for each thread, makes it possible to bring together the flaps, or fix the flaps to the prosthetic material, progressively and stably.

It thus appears evident that if the number of threads used is high, as sometimes happens, at the end of the first step the surgeon will be faced with a complex weave of threads, which have been inserted in the tissues but have not yet been knotted.

Therefore the risk is high of making mistakes during the tying of the knots, for example by inadvertently grasping the ends of two different threads, with evident negative consequences for the successful outcome of the suture (and of the subsequent healing) Furthermore, more generally, it seems evident that it is a very delicate and complex step to keep track of all the different threads simultaneously, without inadvertently tangling them together or in any case managing to work on the right thread without knocking, moving or damaging the other threads.

In order to overcome these drawbacks, use is made of an adapted instrument, called a "suture organizer", which can be arranged in advance around to the wound (e.g., by resting the instrument on the chest of the patient) and which provide the surgeon with a useful guide, during the step of knotting each thread.

Such instruments are in fact constituted by rigid battens, rectangular or curved in plan view, which are placed on the chest of the patient so as to surround at least partially the wound to be sutured.

Above, each batten is provided with a plurality of protrusions arranged in series, arranged between which are blocks made of elastomeric material, so that, laterally, each block is in contact with the walls of the adjacent protrusions.

In each gap defined between contiguous blocks and protrusions it is thus possible to forcibly insert a respective end of a thread, thus ensuring the temporary anchoring thereof to the batten.

Each block (and/or each protrusion) further has an identification code (composed of numbers and/or letters): the surgeon, while inserting each thread into the flaps of tissue, can accommodate the respective ends of that thread on mutually opposite battens, at blocks that have the same code.

Thus, during the subsequent knotting, and after having grasped one end of the thread, the surgeon can immediately identify the other end, even in the tangle of threads that has been created, simply by selecting the end that is anchored to the block that has the same code.

Such implementation solution is not however devoid of drawbacks.

In fact, often the shape and the size of the wound to be sutured, as well as the specific surgical requirements which arise in each instance, are found to be unsuitable for the shape structure of the set of battens that the surgeon has available. If the battens do not adapt (in shape and size) to the structure and to the shape of the wound, then the accommodation of the ends of the thread at the blocks can be inconvenient, to the point that they complicate the suturing activity instead of simplifying it, and/or they impose incorrect paths on the various threads, which are dictated by the incorrect placement of the battens.

Moreover, it is precisely the difficulty of using the instruments described above, for injuries of shape and size which depart appreciably from those that usually need to be sutured in cardiac surgery or thoracotomy operations, that makes the method described above utterly impracticable for very small injuries, such as in mini-thoracotomy operations.

SUMMARY

The aim of the present disclosure is to solve the above mentioned problems, by providing an instrument that can be a valid aid and an effective guide for the surgeon, or in any case for the medical personnel, during the execution of a surgical suture.

Within this aim, the disclosure provides an aiding and guiding instrument for surgical sutures which is versatile and can be used and adapted for injuries of various types, shapes and sizes.

The disclosure also provides an instrument that can be used as an aid and guide for surgical sutures for very small injuries, such as in mini-thoracotomy operations.

The disclosure further provides an instrument that ensures a high reliability of operation.

The disclosure provides an instrument that can be easily implemented using elements and materials that are readily available on the market.

The disclosure further provides an instrument that is low cost and safely applied.

These advantages are achieved by providing an aiding and guiding instrument for surgical sutures, which comprises a frame that can be placed on a patient proximate to a wound to be sutured and/or to flaps of body tissue and/or prosthetic tissue to be mutually fixed, and which defines, on the other side from the area intended to be placed on the patient, a plurality of raised portions arranged in series, at least some of said raised portions being mutually spaced apart in order to define respective accommodation seats for blocks, it being possible, in the gap comprised between each block and each contiguous raised portion, to temporarily stably accommodate a respective portion of a suture thread, characterized in that at least one portion of said frame, associated with said raised portions and with said seats, can be plastically deformed, in order to maintain the shape obtained following a deformation imparted by a user, and the consequent free choice of the shape of said frame, and of the mutual arrangement of said raised portions and of said blocks.

These advantages are also achieved by providing an aiding and guiding kit for surgical sutures, which is provided with a plurality of instruments of the type that comprises a frame that can be placed on a patient proximate to a wound to be sutured and/or to flaps of body tissue and/or prosthetic tissue to be mutually fixed, and which defines, on the other side from the area intended to be placed on the patient, a plurality of raised portions arranged in series, at least some of said raised portions being mutually spaced apart in order to define respective accommodation seats for blocks, it being possible, in the gap comprised between each block and each contiguous raised portion, to temporarily stably accommodate a respective portion of a suture thread, characterized in that each one of said instruments has at least one portion of said frame, associated with said raised portions and with said seats, which can be plastically deformed, in order to maintain the shape obtained following a deformation imparted by a user, and the consequent free choice of the shape of said frame, and of the mutual arrangement of said raised portions and of said blocks.

BRIEF DESCRIPTION OF THE DRAWINGS

Further characteristics and advantages of the disclosure will become better apparent from the description of a preferred, but not exclusive, embodiment of the instrument according to the disclosure, which is illustrated by way of non-limiting example in the accompanying drawings wherein.

DETAILED DESCRIPTION OF THE DRAWINGS

With reference to FIGS. 1-5, the reference numeral 1 generally designates an aiding and guiding instrument for surgical sutures.

More precisely, the instrument 1 is capable, as shall be seen, of facilitating the task of a surgeon (or other suitably qualified personnel) called on to execute on a patient A a surgical suture of the type known as "interrupted", which involves, according to conventional methods, first passing a plurality of suture threads B in sequence through the flaps of tissue (natural or prosthetic) to be brought together.

Subsequently, in order to complete the suture, such surgical technique involves grasping one end of each thread B in order to form with it (and with the other end) a knot (or several knots) and/or a surgical stitch, in order to maintain the flaps in the desired position (brought together) during the process of healing necessary for complete recovery, or in order to fix prosthetic material of various types to body tissues.

It should therefore be noted from this point onward that the instrument 1 according to the disclosure can offer (according to the methods which will be explained below) aid and guidance during interrupted surgical sutures in cardiac surgery or thoracotomy operations, when the substitution or reinforcement of body structures with prosthetic material is made necessary, or the reconstruction or anastomosis of blood vessels, and more generally of the circulatory system (or of other internal organs in the chest cavity).

It will further be made clear that the instrument 1 is also adapted to facilitate suturing in mini-thoracotomy operations, although it should be noted that the possibility is not ruled out of using the instrument 1 according to the disclosure in other application contexts, while remaining within the scope of protection claimed herein.

In any case, the instrument 1 comprises a frame, which can be placed on the patient A proximate to a wound to be sutured and/or to flaps of body tissue and/or prosthetic tissue to be mutually fixed; on the other side from the area intended to be placed on the patient A, the frame defines a plurality of raised portions 2, which are arranged in series.

At least some of the raised portions 2 are further mutually spaced apart, so as to form respective seats between them for accommodating blocks 3 (preferably of matching shape).

Thus, and according to substantially conventional methods, after having placed the instrument 1 on the chest of the patient A, proximate to the wound to be sutured, a corresponding portion of the suture thread B can be temporarily stably accommodated in each gap 4 comprised between each block 3 and the respective contiguous raised portions 2.

More precisely, a first end of a thread B can, for example, be accommodated in each one of the gaps 4, before the thread B is introduced into the flaps of the wound which are to be brought together, or a second end of a thread B can be accommodated therein, after it has passed through the flaps and while waiting for the surgeon to grasp it again in order to tie the desired knot (or knots) with the first end.

According to the disclosure, at least one portion of the frame, which is associated with the raised portions 2 and with the seats (and therefore with the blocks 3), can be plastically deformed.

As is known, in such behavior, which is in contrast with elastic behavior, the deformation (and thus the shape) obtained is held, when the stress that caused it is removed.

Thus, thanks to the use of at least one portion of the frame which can be plastically deformed, following a deformation imparted by a user (the surgeon or other personnel), the frame (or at least the portion thereof mentioned above) maintains the shape obtained, and this evidently makes it possible to freely select (e.g., as a function of the size, shape and type of wound) its shape, and thus the mutual arrangement of the raised portions 2 and of the blocks 3.

In particular, according to a non-limiting embodiment of application of the disclosure, of important practical interest, the frame comprises a casing 5 made of deformable material (e.g., a polymeric material, and preferably polypropylene), which is provided with the raised portions 2 and the seats, in which, as has been seen, the blocks 3 can be accommodated.

Furthermore, the frame comprises a core 6 made of plastically deformable material; the core 6 is stably arranged in the casing 5, so that, following a deformation imparted by the user on the casing 5, the core 6 maintains the shape obtained, and the casing 5, which effectively envelops it, behaves in the same way.

In the preferred embodiment, which is proposed by way of non-limiting example of the application of the disclosure, the casing 5 is constituted substantially by a contoured plate, which is substantially elongated and rectangular in plan.

Figure 1:
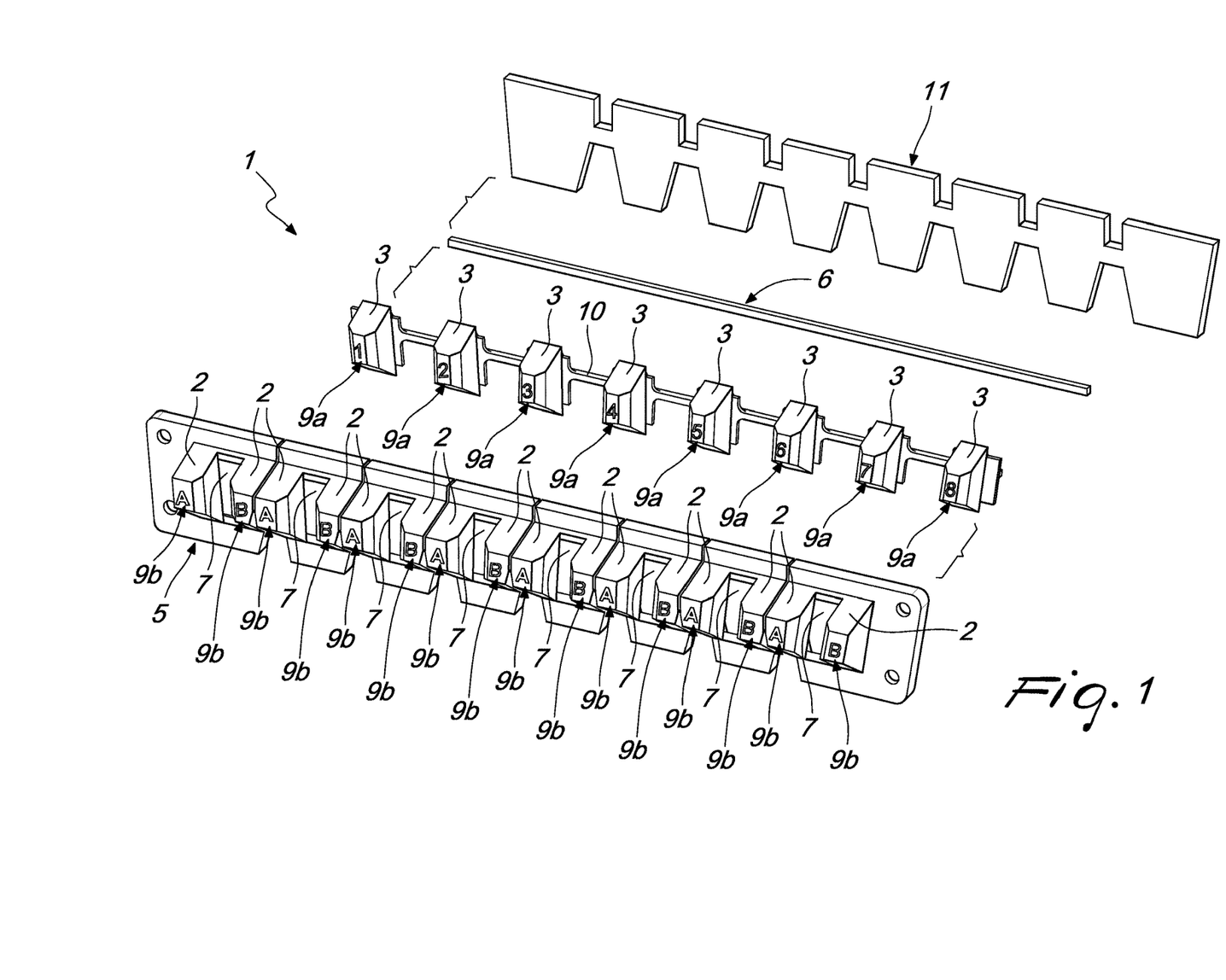
FIG. 1 is a perspective exploded front view of an instrument according to the disclosure, in a first possible shape of the frame.
Figure 2:
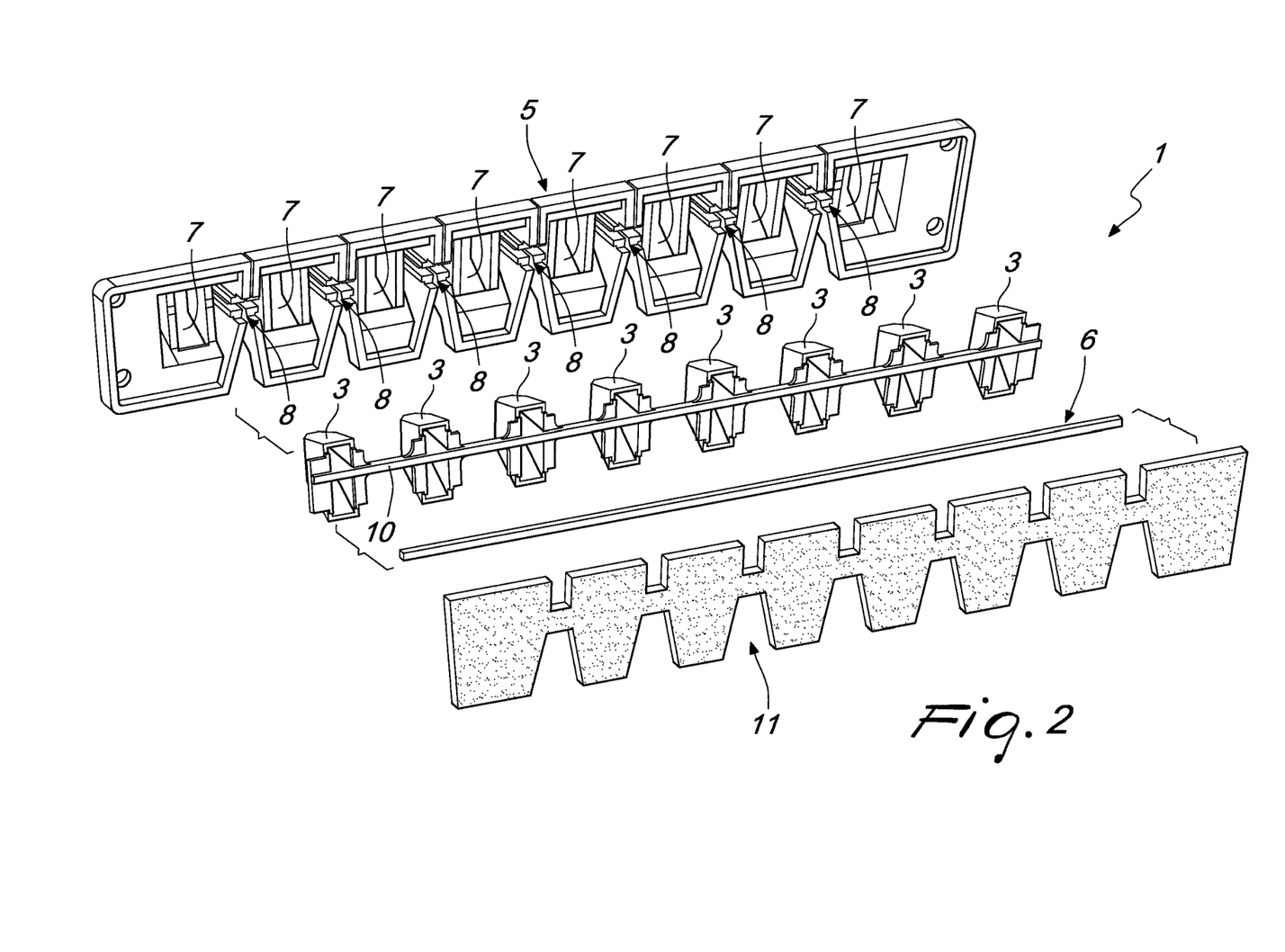
FIG. 2 is a perspective exploded rear view of the instrument according to the disclosure in FIG. 1.
Figure 3:
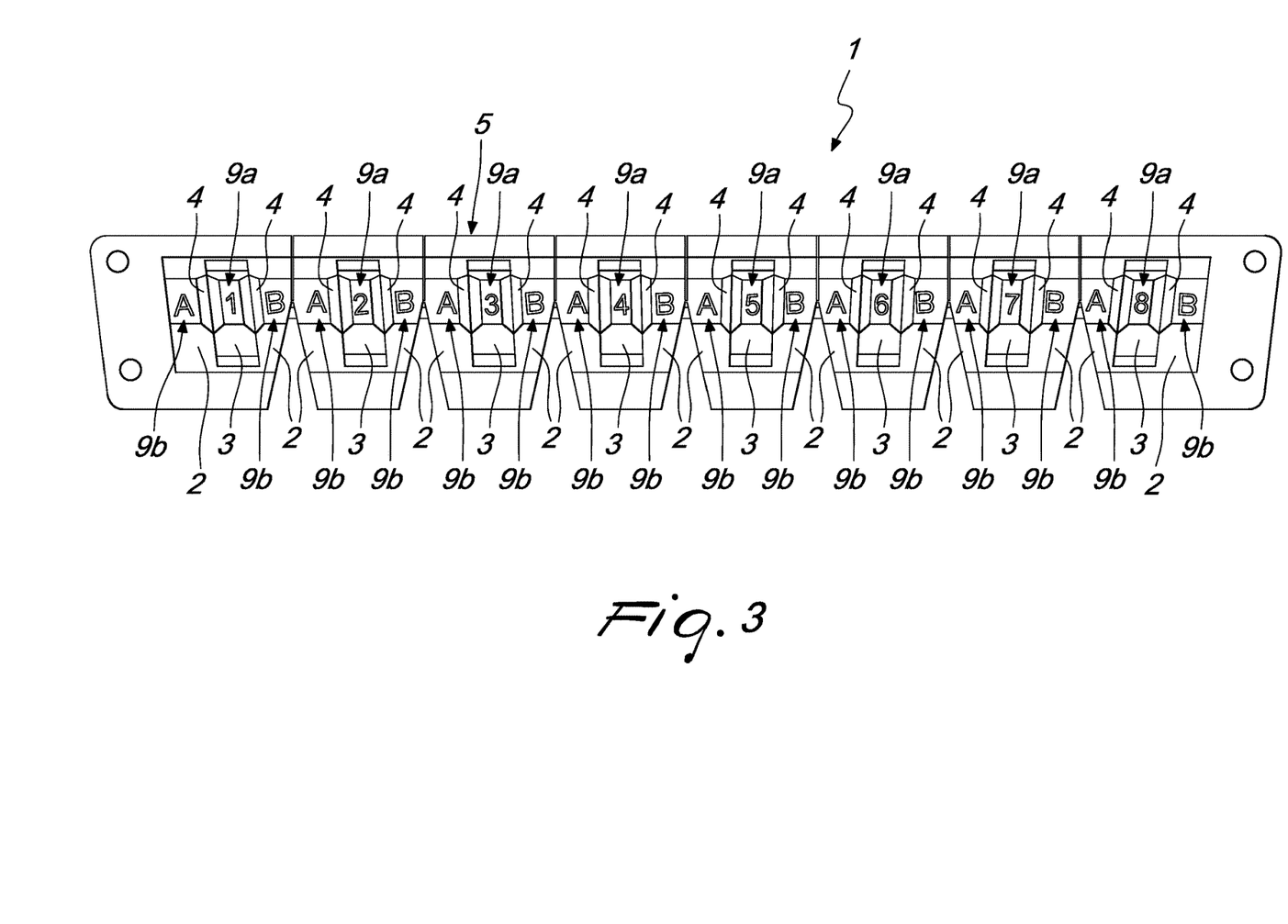
FIG. 3 is a view from above of the instrument according to the disclosure in FIG. 1.
Figure 4:
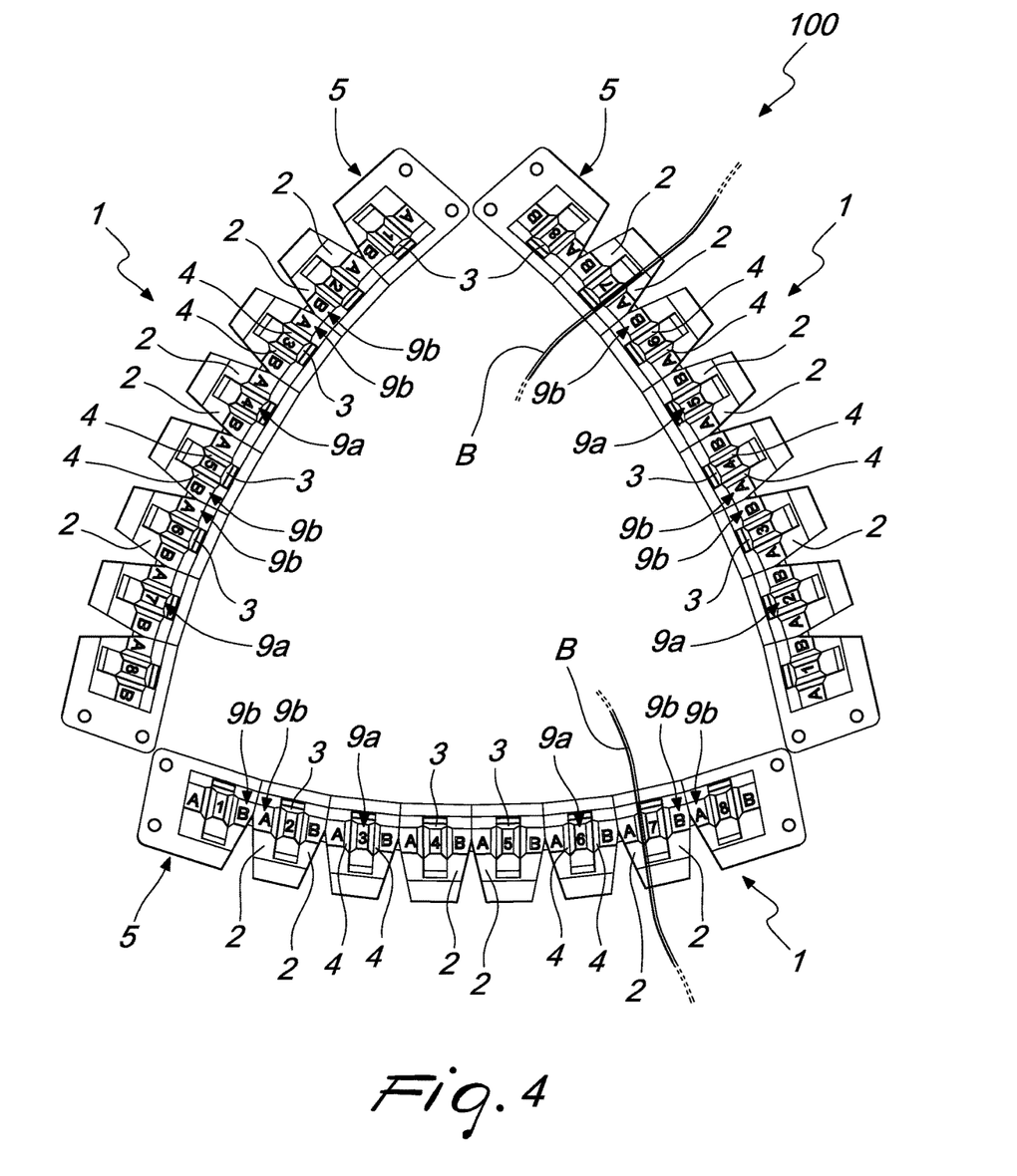
FIG. 4 is a view from above of the kit according to the disclosure, composed of three instruments according to the disclosure, in a second possible shape of the frame.
Figure 5:
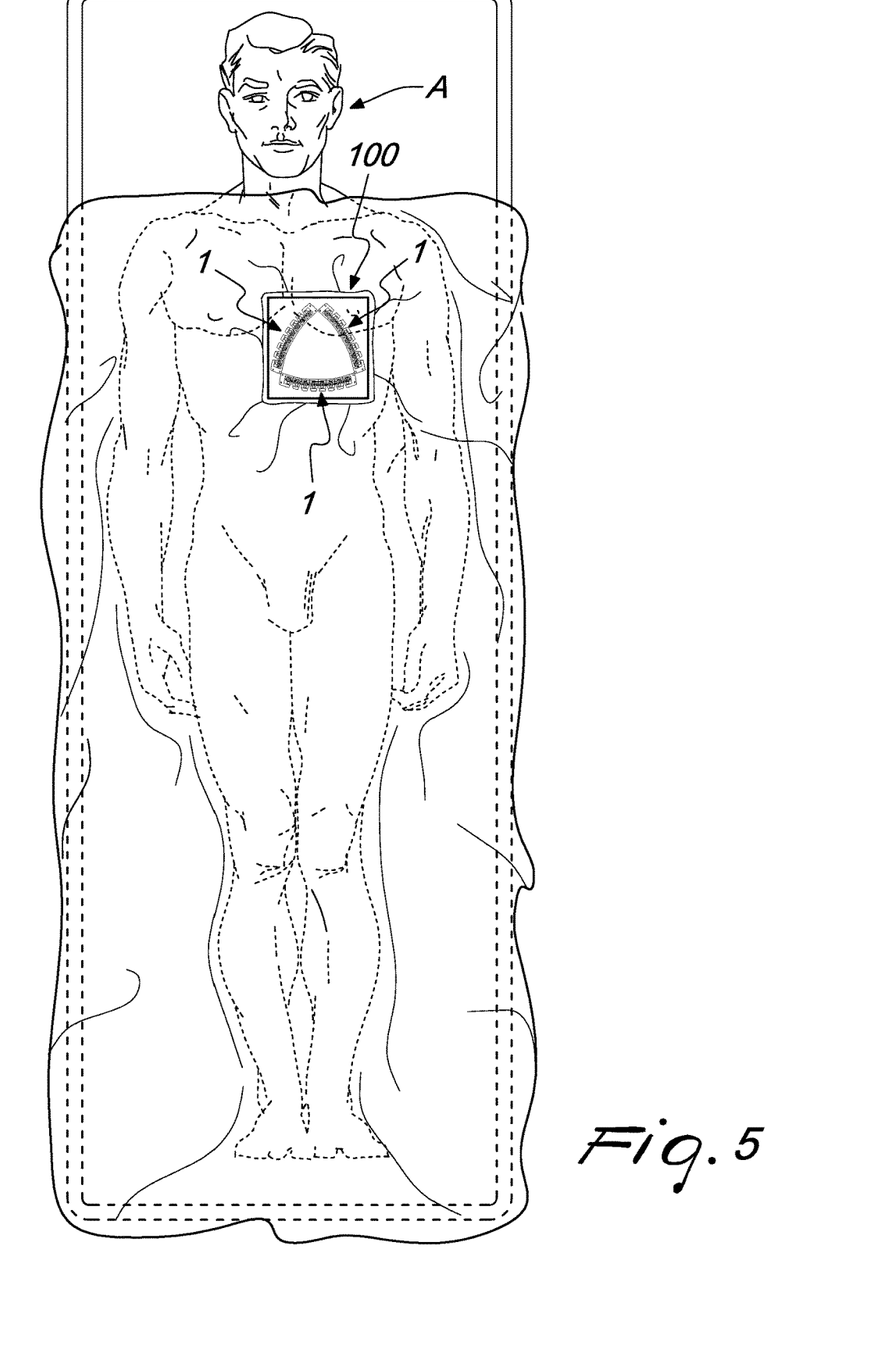
FIG. 5 shows the use of the kit and of the instrument according to the disclosure, for carrying out a surgical suture on a patient.

As is clear, for example, from FIG. 2, the plate is provided with a plurality of longitudinally (i.e. according to the length of the plate) aligned windows 7, which effectively define the above mentioned seats, which accommodate the blocks 3.

Furthermore, between each pair of contiguous windows 7 the plate is folded to form respective pairs of raised portions 2, which face toward corresponding seats (the windows 7).

With further reference to the preferred, but not exclusive, embodiment, the core 6 is constituted by a stem (with a circular or quadrilateral cross-section), which is made of a plastically deformable material: in order to enable the stable placement thereof in the casing 5 (in the plate), the latter is provided with respective longitudinally aligned recesses 8 (which can be seen in FIG. 2).

In order to obtain the desired behavior (maintenance of the deformation when the stress that caused it is removed), the core 6 (the stem) is made of a plastically deformable material selected from among gold, silver, platinum, iron, nickel, copper, aluminum, zinc, tin, lead; preferably, the core 6 is made of aluminum Conveniently, in the preferred embodiment each block 3 has a substantially parallelepiped base, with a transverse cross-section substantially complementary to each one of the windows 7 (in order to allow the accommodation of each block 3 in the respective seat).

Furthermore, substantially on the opposite side with respect to the window 7 and to the plate, each block 3 has an end portion with a progressively decreasing transverse cross-section, which bears on its top a first identification code 9a (therefore immediately visible to the surgeon, when the instrument 1 is placed on the chest of the patient A).

With the block 3 accommodated in the respective seat (window 7), two mutually opposite walls of the substantially parallelepiped base come into contact, abutting elastically, with respective contiguous raised portions 2, which in turn are marked by a second identification code 9b.

Thus, a corresponding gap 4 is defined right between one of the walls and the respective raised portion 2 (against which the wall abuts elastically), in which a respective portion of a suture thread B can be temporarily stably accommodated.

Precisely in order to allow the elastic abutment, each block 3 is made of an elastomeric material, and preferably of rubber. Conveniently each base of the respective block 3 is coupled to the corresponding base of the adjacent block 3 by way of a corresponding connecting shank 10, which is accommodated in the recesses 8 defined by the plate.

Thanks to the shank 10 (which is also made of rubber or other elastomeric material), all the blocks 3 are joined in a single component (as can be seen clearly, for example, in FIG. 2), and this simplifies the operations to assemble the instrument 1 and ensures an optimal anchoring of the blocks 3 to the plate, at the windows 7.

Advantageously, the plate is closed by a conveniently contoured strip 12, which is arranged on the opposite side with respect to the raised portions 2 and is intended to be placed on the patient A: thus, the strip 12 helps prevent the stem and the shank 10, which are accommodated in the recesses 8, from protruding from these recesses and/or from being moved from the selected position.

Preferably, the strip 11 is made of double sided adhesive felt: thus, when the instrument 1 is arranged on the chest of the patient A, its outward-facing side can adhere to the skin of the patient A, thus guarding against the danger that during the suture the instrument 1 could be accidentally moved.

Likewise, the choice to make the inner face of the strip 11 from adhesive material facilitates stable coupling to the plate.

It should be noted therefore that the instrument 1 according to the disclosure can be sold individually, in order to then be used in the non-deformed shape structure, or conveniently curved or folded, at a wound to be sutured.

Moreover, in the preferred use around the wound to be sutured, it is usually necessary to deploy two or more instruments 1 according to the disclosure (as in FIGS. 4 and 5), so as to at least partially surround the wound and be able to anchor a first end of each suture thread B to a gap 4 of a first instrument 1 and the second end, at the other end from the first, to a gap 4 of a second instrument 1 (which faces toward the first instrument 1 on the opposite side with respect to the wound), which are identified by the same codes 9a, 9b.

Thus the present discussion also relates to an aiding and guiding kit 100 for surgical sutures, which is provided with a plurality of instruments 1 of the type described in the foregoing pages: each instrument 1 included in the kit 100 thus comprises first of all a frame that can be placed on a patient A proximate to a wound to be sutured and/or to flaps of body tissue and/or prosthetic tissue to be mutually fixed.

The frame of each instrument 1 in turn defines, on the other side from the area intended to be placed on the patient A, a plurality of raised portions 2 which are arranged in series. At least some of the raised portions 2 are mutually spaced apart, so as to define respective seats for accommodating blocks 3 of matching shape.

The gap 4 comprised between each block 3 and each contiguous raised portion 2 can thus temporarily stably accommodate a respective portion of a suture thread B.

According to the disclosure, each instrument 1 included in the kit 100 has at least one portion of the frame, associated with the raised portions 2 and with the seats, and can be plastically deformed. This makes it possible, as has previously been seen, to maintain the shape obtained following a deformation imparted by a user, and consequently ensure the possibility to freely select the shape of the frame, and of the mutual arrangement of the raised portions 2 and of the blocks 3.

Use of the instrument (and of the kit) according to the disclosure is the following.

Faced with the necessity to carry out an interrupted surgical suture (or possibly a suture of another type), the surgeon can arrange the instruments 1 according to the disclosure around the wound, making them adhere to the chest (or other part of the body) of the patient A at the area of contact of the frame, where the strip 11 of adhesive material is also present.

Thus, while suture threads B are progressively introduced, and are passed through the flaps of the wound, the respective mutually opposite ends can be stably anchored in the gaps 4, which are defined between the blocks 3 and the respective contiguous raised portions 2.

More precisely, as has been seen, the surgeon can anchor the two ends of the same thread B at gaps 4 defined between blocks 3 and raised portions 2 of instruments 1 which are mutually opposite, but which bear the same codes 9a, 9b. In this manner, during the subsequent knotting of the threads B, which is evidently necessary to the completion of the suture, the surgeon can immediately identify the ends belonging to the same thread B, thus correctly executing the knot and/or the stitch and preventing mistakes and unwanted tangles.

In order to ensure an optimal identification, different forms of encoding can be adopted for the codes 9a, 9b, for example by marking the blocks 3 of each instrument 1 with first codes 9a which are constituted by letters in alphabetical order, and the raised portions 2 with second codes 9b corresponding to progressively-increasing numbers (or vice versa). In this manner, each gap 4 is identified by a short character string made up of a letter (the first code 9a) and a number (the second code 9b).

Moreover, the possibility is not excluded of adopting different encoding methods and/or of marking only the blocks 3 or only the raised portions 2.

In any case, as has been seen the choice to use a core 6 made of plastically deformable material makes it possible to freely select the shape to be given to the instrument 1, so as to adapt the arrangement of the various gaps 4 to the shape of the wound, and in general to the needs of the specific case.

With reference, for example, to the preferred solution described in the foregoing pages, in the non-deformed configuration the plate is rectangular in shape (as in FIGS. 1, 2 and 3), and can therefore be placed thusly on the chest of the patient A, so as to have a plurality of gaps 4 available (in which to stably place respective ends of threads B), which are aligned along a straight line.

If required by the circumstances, the surgeon (or other qualified personnel) can easily bend the plate, curving it, so as to bring the various blocks 3 and raised portions 2 (and with them the gaps 4), so as to arrange them according to a curved line (as in FIGS. 4 and 5), which can be selected at will, as a function of the size and of the shape of the wound.

The instrument 1 thus offers a valid aid and an effective guide for the surgeon, or in any case for the medical personnel, during the execution of the surgical suture, while at the same time being extremely versatile, in that it can be used and adapted for injuries of various different types, shapes and sizes.

This makes it possible not only to use the instrument 1 (and/or the kit 100) for cardiac surgery or thoracotomy operations, but also for mini-thoracotomy operations (when the injuries are very small), and more besides, according to the specific applicative requirements.

In practice it has been found that the instrument and the kit according to the disclosure fully achieve the set advantages, in that, by making at least one portion of the frame from plastically deformable material, such portion being associated with the raised portions and with the seats, which accommodate the blocks which together with the raised portions define the gaps in which the suture threads are accommodated, it is possible to maintain the shape obtained following a deformation imparted by a user, and thus to freely select the mutual arrangement of the raised portions and of the blocks, thus obtaining an instrument that is a valid aid and an effective guide for the surgeon, or in any case for the medical personnel, during the execution of a surgical suture.

The disclosure, thus conceived, is susceptible of numerous modifications and variations. Moreover, all the details may be substituted by other, technically equivalent elements.

In the embodiments illustrated, individual characteristics shown in relation to specific examples may in reality be substituted with other, different characteristics, existing in other embodiments.

In practice, the materials employed, as well as the dimensions, may be any according to requirements and to the state of the art.

The invention claimed is:

1. An aiding and guiding instrument for surgical sutures, the instrument comprising:
   a frame configured to be placed on a patient, said frame defines a plurality of raised portions arranged in series, at least some of said raised portions being mutually spaced apart to define a plurality of accommodation seats for blocks and a block disposed in each one of the accommodation seats
   wherein in a gap comprised between each block and each contiguous raised portion, a respective portion of a suture thread is temporarily stably accommodated, wherein at least one portion of said frame, associated with said raised portions and with said seats, can be plastically deformed, to maintain a shape obtained following a deformation imparted by a user, and the shape of said frame, and of the mutual arrangement of said raised portions and of said blocks,
   wherein said frame comprises a casing made of deformable material provided with said raised portions and said seats, and a core made of plastically deformable material stably arranged in said casing, following a deformation imparted by a user on said casing, said core, and said casing, configured to maintain the shape,
   wherein said casing is constituted substantially by a contoured plate and has a plurality of longitudinally aligned windows, which define said seats, between each contiguous pair of said windows said plate being folded so as to define respective pairs of said raised portions, which face toward corresponding said seats,
   wherein each of said blocks has a substantially parallelepiped base, with a transverse cross-section substantially complementary to each one of said windows, and an end portion with a progressively decreasing transverse cross-section, having a first identification code, two mutually opposite walls of said substantially parallelepiped base abutting elastically against contiguous respective said raised portions, which are marked by a second identification code, for temporary stably accommodating a portion of a suture thread in a corresponding gap defined between one of said walls and the corresponding said raised portion.

2. The instrument according to claim 1, wherein said core is constituted by a stem made of a plastically deformable material, said plate being provided with respective longitudinally aligned recesses configured for the stable placement of said stem.

3. The instrument according to claim 1, wherein said base of each one of said blocks is coupled to a corresponding base of an adjacent block by way of a corresponding connecting shank, which is accommodated in said recesses which are defined by said plate.

4. An aiding and guiding instrument for surgical sutures, the instrument comprising:
a frame configured to be placed on a patient, said frame defines a plurality of raised portions arranged in series, at least some of said raised portions being mutually spaced apart to define a plurality of accommodation seats for blocks and a block disposed in each one of the accommodation seats,
wherein in a gap comprised between each block and each contiguous raised portion, a respective portion of a suture thread is temporarily stably accommodated, wherein at least one portion of said frame, associated with said raised portions and with said seats, can be plastically deformed, to maintain a shape obtained following a deformation imparted by a user, and the shape of said frame, and of the mutual arrangement of said raised portions and of said blocks,
wherein said frame comprises a casing made of deformable material provided with said raised portions and said seats, and a core made of plastically deformable material stably arranged in said casing, following a deformation imparted by a user on said casing, said core, and said casing, configured to maintain the shape,
wherein said casing is constituted substantially by a contoured plate and has a plurality of longitudinally aligned windows, which define said seats, between each contiguous pair of said windows said plate being folded so as to define respective pairs of said raised portions, which face toward corresponding said seats, wherein said plate is closed by a strip arranged on an opposite side with respect to said raised portions and is configured to rest on the patient.

5. The instrument according to claim 1, wherein said core is made of a plastically deformable material selected from gold, silver, platinum, iron, nickel, copper, aluminum, zinc, tin, and lead.

6. The instrument according to claim 4, wherein said casing is made of a polymeric material, each one of said blocks being made of an elastomeric material, said strip being made of double sided adhesive felt.

7. An aiding and guiding kit for surgical sutures, said kit comprising:
a plurality of instruments comprising a frame configured to be placed on a patient, said frame defines a plurality of raised portions arranged in series, at least some of said raised portions being mutually spaced apart to define a plurality of accommodation seats for blocks and a block disposed in each one of the accommodation seats, wherein in a gap comprised between each block and each contiguous raised portion, a respective portion of a suture thread is temporarily stably accommodated, wherein each one of said instruments has at least one portion of said frame, associated with said raised portions and with said seats, which can be plastically deformed, to maintain the shape obtained following a deformation imparted by a user, and a shape of said frame, and of the mutual arrangement of said raised portions and of said blocks,
wherein said frame comprises a casing made of deformable material provided with said raised portions and said seats, and a core made of plastically deformable material stably arranged in said casing, following a deformation imparted by a user on said casing, said core, and said casing, configured to maintain the shape,
wherein said casing is constituted substantially by a contoured plate and has a plurality of longitudinally aligned windows, which define said seats, between each contiguous pair of said windows said plate being folded so as to define respective pairs of said raised portions, which face toward corresponding said seats, wherein said plate is closed by a strip arranged on an opposite side with respect to said raised portions and is configured to rest on the patient.

8. The instrument according to claim 4, wherein said core is constituted by a stem made of a plastically deformable material, said plate being provided with respective longitudinally aligned recesses configured for the stable placement of said stem.

9. The instrument according to claim 4, wherein said core is made of a plastically deformable material selected from gold, silver, platinum, iron, nickel, copper, aluminum, zinc, tin, and lead.

\* \* \* \* \*